United States Patent [19]

Renner

[11] 3,981,845
[45] Sept. 21, 1976

[54] HIGH SURFACE AREA POLYCONDENSATION POLYMER PARTICULATES BASED ON UREA AND FORMALDEHYDE

[75] Inventor: Alfred Renner, Muenchenstein, Switzerland

[73] Assignee: Ciba-Geigy AG, Basel, Switzerland

[22] Filed: May 27, 1975

[21] Appl. No.: 580,792

Related U.S. Application Data

[60] Continuation of Ser. No. 442,901, Feb. 15, 1974, abandoned, which is a continuation-in-part of Ser. No. 380,127, July 17, 1973, abandoned, which is a continuation of Ser. No. 275,658, July 27, 1972, abandoned, which is a continuation-in-part of Ser. Nos. 102,170, Dec. 28, 1970, abandoned, and Ser. No. 83,624, Oct. 23, 1970, abandoned, said Ser. No. 102,170, is a division of Ser. No. 389,197, Aug. 12, 1964, abandoned, and Ser. No. 775,964, Nov. 14, 1968, Pat. No. 3,553,115, which is a continuation-in-part of Ser. No. 807,926, March 17, 1969, abandoned.

[30] Foreign Application Priority Data

Aug. 23, 1963  Switzerland.................... 10437/63
Mar. 21, 1968  Switzerland.................... 04169/68

[52] U.S. Cl........................... 260/69 R; 106/288 Q; 260/15; 260/71
[51] Int. Cl.$^2$............................ C08G 12/12
[58] Field of Search......................... 260/69 R, 71

[56] References Cited
UNITED STATES PATENTS

| | | | |
|---|---|---|---|
| 3,198,761 | 8/1965 | O'Donnell | 260/69 |
| 3,238,156 | 3/1966 | Kohrn | 260/2.5 |
| 3,428,607 | 2/1969 | Renner | 260/67.6 |
| 3,553,115 | 1/1971 | Curchod et al. | 260/3 |
| 3,737,404 | 6/1973 | Berstein | 260/39 R |

*Primary Examiner*—Edward M. Woodberry
*Attorney, Agent, or Firm*—Wenderoth, Lind & Ponack

[57] ABSTRACT

A highly dispersed solid non-porous insoluble and infusible urea-formaldehyde condensation polymer in the form of a fluffy white powder, said product having a specific surface area of more than 10 square meters per gram and an average particle size smaller than 5 microns. The product preferably essentially consists of approximately spherical microparticles having substantially uniform size and shape and shows a tendency to form loosely agglomerated structures. These solids are useful as rubber reinforcing agents and as paper pigmentary fillers.

5 Claims, No Drawings

HIGH SURFACE AREA POLYCONDENSATION POLYMER PARTICULATES BASED ON UREA AND FORMALDEHYDE

CROSS-REFERENCES TO RELATED APPLICATIONS

This application is a continuation of application Ser. No. 442,901 filed Feb. 15, 1974, now abandoned, which is a continuation-in-part application of application Ser. No. 380,127, filed July 17, 1973 (now abandoned), which application is a continuation of application Ser. No. 275,658, filed July 27, 1972 (now abandoned), the latter application being a combined continuation-in-part application of a. copending application Ser. No. 102,170, filed Dec. 28, 1970 (now abandoned), which in turn is a divisional application of application Ser. No. 389,197, filed Aug. 12, 1964 (now abandoned), and of application Ser. No. 775,964, filed Nov. 14, 1968, now U.S. Pat. No. 3,553,115, which in turn is a continuation-in-part application of application Ser. No. 389,197, filed Aug. 12, 1964 (now abandoned), and b. copending application Ser. No. 83,624, filed Oct. 23, 1970 (now abandoned), which in turn is a continuation-in-part application of copending application Ser. No. 807,926, filed Mar. 17, 1969 (now abandoned).

The instant invention provides novel highly dispersed solid insoluble and infusible urea-formaldehyde condensation polymer particulates in the form of a fluffy white powder, said product having a specific surface area of more than 10 square meters per gram, said product essentially consisting of approximately spherical microparticles having substantially uniform size and shape and showing a tendency to form agglomerated structures, e.g., like grapes or like pearls in a string, said approximately spherical microparticles having an average diameter smaller than 5 micron.

The agglomerated structures in general have a average diameter of up to 10 microns. Often the microparticles are loosely agglomerated.

The novel highly disperse, insoluble and infusible urea formaldehyde polycondensation products are inter alia suitable for use as reinforcing fillers for elastomers such as natural or synthetic rubber and as paper pigmentary fillers.

The products of the present invention can be obtained by reacting urea and formaldehyde or a precondensate thereof in the presence of sulphamic acid. This process permits the reaction to proceed without the requisite for having any modifying agent such as surface active agents or protective colloids present.

The present urea-formaldehyde polymers may further be obtained by curing or condensing respectively in the presence of surface-active substances of the non-ionic or ionic kind, for example non-ionic polyalkylene ethers or natural products, such as tragacanth, 20 to 30 m²/g, and consist of approximately spherical microparticles. Such products are especially well adapted as paper pigmentary fillers.

Particularly suitable Brönsted acids are also sulphamic acid (amidosulphonic acid $H_2N-SO_3H$), and water-soluble ammonium hydrogen sulphates of general formula

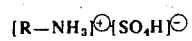

wherein R denotes a hydrogen atom or an organic radical which does not impair the solubility in water, such as especially an alkyl, cycloalkyl, hydroxyalkyl, aralkyl or aryl radical.

Examples of optionally substituted ammonium hydrogen sulphates are, in addition to $NH_4^\oplus \cdot HSO_4^\ominus$; $CH_3-NH_3^\oplus \cdot HSO_4^\ominus$; $C_2H_5NH_3^\oplus \cdot HSO_4^\ominus$; $HO-CH_2CH_2-NH_3^\oplus \cdot HSO_4^\ominus$

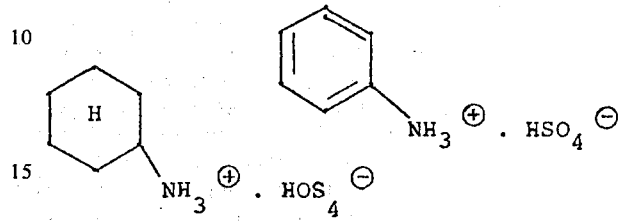

Where the basicity of the amine component is too great, it is appropriate to add a little excess sulphuric acid to the ammonium salt solution. Typical highly dispersed solid, insoluble, infusible urea-formaldehyde condensation polymers obtained utilizing as the Bronsted acid, sulphamic acid or the above-mentioned water-soluble ammonium hydrogen sulphates in the presence of a protective colloid have a specific surface area of about 40 to 70 m²/g and consist of approximately spherical primary microparticles having an average diameter from about 400 to about 450 A. units.

Such products are especially suitable as rubber reinforcing agents.

In preparing the products of the invention, the molar ratio to be used is more than 1.2 mols, and preferably about 1.5 mols of formaldehyde per 1 mol of urea. The use of more than 2 mols of formaldehyde per 1 mol of urea, whilst not being inoperative, is uneconomical.

If desired, a precondensate of urea and less than the total amount of $CH_2O$ required (for example 1 mol of $CH_2O$ per 1 mol of urea) can first be manufactured and the remaining quantity of formaldehyde added on subsequent gelling.

The precondensate is appropriately manufactured in the pH range of between 6 and 9 and in the temperature range of between 40° and 100°C. The reaction time should appropriately be so long that the greater part of the formaldehyde (about 90%) has the opportunity of reacting with the urea, but not so long that the water tolerance of the precondensate becomes so low that it can no longer be homogeneously mixed with the acid solution. Relatively high temperatures and relatively low pH values lead more rapidly to the desired degree of polycondensation. The concentrations of urea and formaldehyde are selected preferably so that the concentration of the precondensate is in the optimum range of about 25% by weight. Appropriately, the protective colloid is added to the precondensate in any stage of its manufacture; it is, however, also possible, without disadvantage, to prepare a solution of the protective colloid separately and only to add this to the finished precondensate solution before the gel formation. By protective colloids there are understood, in this context, water-soluble macromolecular substances which greatly increase the viscosity of aqueous solutions. Typical representatives of this class of compounds are the sodium salt of carboxymethylcellulose, methylcellulose, ethylcellulose and β-hydroxyethylcellulose, polyvinyl alcohol, and water-soluble polymers and copolymers of acrylic or methacrylic acid. The concentrations at which these substances develop their best effect depend on their chemical structure and on their molecular weight. They are generally effective in amounts of between 0.1% and 10%, preferably between 0.5 and 5%, relative to the weight or urea and formaldehyde.

The gel formation is brought about by mixing the precondensate with a solution of the Brönsted acid, e.g., the amidosulphonic acid or of optionally substituted ammonium hydrogen sulphates at temperatures of between room temperature and 100°C. If the strength of the acid and the temperature are chosen correctly, the gel formation starts within a few seconds. Intensive brief mixing of the precondensate and acid solution must therefore be provided; continuous mixing of the two solutions is particularly appropriate for this purpose. The gel formation is weakly exothermic - the heat capacity of the reaction mixture, however, easily sufficies to absorb the heat of reaction, which as a rule causes a temperature rise of 10° – 15°C, under adiabatic conditions.

Despite its high water content the gel is dimensionally stable. It can be easily comminuted, for example by means of an extruder or of a cutter-granulator. After comminution the gel can be rendered neutral in an aqueous suspension. It is filtered off or centrifuged off and optionally washed in order to remove inorganic salt. After drying and cooling the solid infusible and insoluble polycondensation product is deagglomerated by means of a pin mill or jet mill.

Conventional urea formaldehyde resins and relating conventional processes for the manufacture of those resins are disclosed in the following specifications:

U.S. Pat. No. 2,797,201
U.S. Pat. No. 3,238,156
U.S. Pat. No. 3,198,761
U.S. Pat. No. 3,118,849
U.S. Pat. No. 2,377,867

These conventional resins are either in solution form or they are of very small specific surface area.

In the conventional processes for the manufacture of condensation products from urea and formaldehyde it is usual to ensure by suitable measures — for example by discontinuing the resinification reaction before term or by reaction the components within a pH range from 5 to 10 — that products are obtained which are soluble or insoluble, or at least still fusible, so that they can be shaped and cured in a follow-up stage. In contradistinction thereto the insoluble, infusible urea formaldehyde polymers can no longer be shaped and at the same time cured.

As used herein the term "insoluble" means that the products are not soluble in the conventional organic polymer solvents such as for example alcohols, ethers, ketones, hydrocarbons, and the like. The products of the invention melt only under conditions of decomposition and are thus designated herein as "infusible".

In the examples which follow the parts denote parts by weight and the percentages denote percentages by weight. The relationship between parts by volume and parts by weight is the same as that between the milliliter and the gram.

A. Examples according to the invention

EXAMPLE 1

6.3 parts of a high molecular sodium carboxymethylcellulose are dissolved in 315 parts of water, 450 parts of 30% strength aqueous formaldehyde solution are added, and the mixture is adjusted to pH = 7 with dilute sodium hydroxide solution and warmed to 70°C. 180 parts of urea are added and condensation effected for 3 hours at pH = 7° and 70°C.

The precondensate thus obtained is cooled to 50°C and rapidly mixed with a solution of 9.7 parts of sulphamic acid in 300 parts of water which has also been warmed to 50°C. Gel formation starts after 12 seconds and the temperature rises to 60°–65°C. The gel is left at this temperature for 3 hours. At the commencement of the gelation of the pH value is 1.5; at the conclusion it is 1.8. The obtained product is comminuted in a cutting granulator, suspended in 1 to 2 times its amount of water, centrifuged off, washed and dried at 80°C in a stream of air. After cooling the product is deagglomerated by grinding in a pin mill.

230 parts of a white powder having a bulk density of about 77 g/litre and a specific gravity of 1.46 g/cm$^3$ are obtained. The electron-microscope picture shows approximately spherical single particles of average diameter of 400 A. The specific surface area of the particles is 72 m$^2$/g.

EXAMPLES 2 – 9

In the following Examples highly disperse crosslinked urea-formaldehyde polycondensation products are prepared by gelling with different acids a 25% strength aqueous solution of a precondensate of urea and formaldehyde at a pH value smaller than 4.

The precondensate used in the following Examples is prepared as follows:

2.1 parts of a high molecular sodium carboxymethylcellulose are dissolved in 105 parts of water, 150 parts of 30% strength aqueous formaldehyde solution (1.5 mol) are added, and the mixture is adjusted to pH = 7 with dilute sodium hydroxide solution and warmed to 70°C. 60 parts of urea are added and condensation effected for 2 hours at pH = 7° and 70°C. For the gelation of the precondensate the amount of acid as indicated in the following Table is dissolved in water till 103 parts are resulted.

The polycondensation products are prepared and worked-up under the same reaction conditions as described in Example 1.

Table 1

| Example | Acid | Amount of the used acid (0.033 mol) | Gelation initial pH-value | pH value after 2 h | Yield (g) | Bulk density (g/l) | Specific surface area (m$^2$/g) |
| --- | --- | --- | --- | --- | --- | --- | --- |
| 2 | hydrochloric acid | 33 ml (1n) | 1.8 | 1.3 | 75 | 71 | 29 |
| 3 | nitric acid | 17 ml (2n) | 2.7 | 3.9 | 75 | 67 | 25 |
| 4 | phosphoric acid | 3.8 g (85%) | 3.0 | 3.7 | 73 | 111 | 28 |
| 5 | formic acid | 1.5 g | 3.0 | 3.18 | 66 | | 39 |
| 6 | exalic acid | 4.2 g (71%) | 2.2 | 2.28 | 72 | 69 | 43 |
| 7 | maleic anhydride | 3.3 g | 2.1 | 2.90 | 75 | 116 | 43 |
| 8 | sulphamic | | | | | | |

Table 1-continued

| Example | Acid | Amount of the used acid (0.033 mol) | Gelation initial pH-value | pH value after 2 h | Yield (g) | Bulk density (g/l) | Specific surface area (m²/g) |
|---|---|---|---|---|---|---|---|
| 9 | acid sulphuric acid | 3.2 g | 1.5 | 1.80 | 78 | 156 | 58 |
|  |  | 33 ml (2n) | 1.4 | 1.70 | 77 | 69 | 29 |

EXAMPLE 10

60 parts of urea are dissolved at room temperature in 200 parts of an aqueous 30% formaldehyde solution, then diluted with 31.4 parts of a 25% aqueous solution of the dispersant "Emulphor O", 109.5 parts of a 50% aqueous solution of monobasic monoethanolamine phosphate and 238 parts of water, and then adjested with 85.6 parts by volume of dilute hydrochloric acid (1 part by volume of concentrated hydrochloric acid to 1 part of water) at 20°C to a pH value of 1.0. The batch is heated for 6 hours at 45°C; the resulting, firm, white gel is then comminuted with a stirrer with 1100 parts of water and 138 parts by volume of concentrated ammonia until it forms a white paste having a pH of 8.0. The whole is kept for 10 hours at room temperature, filtered and washed with water until chlorine ions can no longer be detected in the filtrate. The moist filter cake is subjected to azeotropic distillation with benzene until water no longer separates, whereupon the bulk of the benzene is filtered off. The white, pulverulent resin is freed from benzene in a drying cabinet at 80°C until its weight remains constant, to a white powder which is ground for 4 hours in a porcelain ball mill. The resulting ground material passes through a sieve having an inner mesh size of 0.1 mm. Yield: 49 parts of a white powder which has a bulk weight of 115 g/l and a specific surface area of 73 m²/gram.

The rebound resilience values shown in the following Examples were determined with the aid of the test gear of the Institut Francais du Caoutchouc (makers: Mecanique Industrielle d'Enghien) whose pendulum has an energy content of 5 cm. kg. (at 90° amplitude) and strikes from an amplitude of 90° two discs of 4.5 mm thickness and 44.6 mm diameter placed one on top of the other. The rebound of the pendulum is expressed in percent of the recovered energy content. In the static test to determine the hysteresis and resilience the test piece is made to French Standard Specification NFT 43–002 as a ring having an external diameter of 52.6 ± 0.2 mm, an internal diameter of 44.6 ± 0.2 mm thickness. The relevant tensile stress test is performed according to French Standard Specification NFT 46–002, the stress-strain diagram being plotted to a stretch of 300%.

Vulcanizing natural rubber in the presence of the urea-formaldehyde polycondensate according to Example 10

A 2-roll mill is used for preparing a mixture from 100 parts of natural rubber, 2 parts of stearic acid, 5 parts of zinc oxide, 30 parts of the finely divided aminoplast described above, 3 parts of the plasticiser marketed by Messrs. Sun Oil Co. under the registered trademark "Circolight Process Oil" (a naphthenic petroleum fraction having a flash point of 165°C and containing 19% of aromatic carbon atoms, 40% of naphthenic carbon atoms and 41% of paraffinic carbon atoms), 2.3 parts of sulfur, 0.8 parts of the vulcanization accelerator marked by Messrs. Monsanto under the registered trademark "Santocure" (consisting of N-cyclohexyl-2-benzothiazolesulfenamide) and 0.3 parts of zinc diethyl dithiocarbamate. The light-colored, homogeneous test pieces obtained by vulcanization at 143°C revealed the following properties:

Table 2

| | |
|---|---|
| Vulcanization time minutes | 15 |
| Tensile strength ASTM D 412, kg/cm² | 240 |
| Modulus at 300% stretch ASTM D 412, kg/cm | 117 |
| Ultimate stretch ASTM D 412, percent | 500 |
| Shore hardness A | 71 |
| Tear strength ASTM D 624, test piece A, kg/cm | 98 |
| Rebound resilience percent | 51 |
| Abrasion (French Standard Specification NFT 46-012) cu.cm/HP/hour | 879 |

For comparison natural rubber, filler by a typical optimum receipe with carbon black and with silic acid aerogel respectively, was vulcanized, using the following two mixes:

Table 3

| | Mix I parts | Mix II parts |
|---|---|---|
| Natural rubber, smoked sheets | 100 | 100 |
| Stearic acid | 2 | 2 |
| Zinc oxide | 5 | 5 |
| "Vulcan 6" +) | 47 | — |
| "Hisil 233" ++) | — | 54 |
| Pine tar | 3 | — |
| Diethyleneglycol | — | 2 |
| Sulfur | 2.5 | 2.5 |
| "Santocure" | 0.7 | 0.8 |
| Zinc diethyl dithiocarbamate | — | 0.2 |

+) "Vulcan 6" is the registered trademark of a carbon black marketed by Messrs. Cabot
++) "Hisil 233" is the registered trademark of a silica gel marketed by messrs. Columbia Southern Chemical Corporation.

The above mixes were vulcanized at the optimum temperature of 143°C. The test pieces revealed the following properties:

Table 4

| | | |
|---|---|---|
| Vulcanization time, minutes | 20 | 15 |
| Tensile strength, kg/cm² | 510 | 233 |
| Modulus at 300% elongation, kg/cm² | 112 | 57 |
| Ultimate elongation, percent | 575 | 650 |
| Shore hardness A | 63 | 74 |
| Tear strength, kg/cm | 147 | 129 |
| Rebound resilience, percent | 35 | 36 |
| Abrasion cu.cm/HP/hour | 273 | 836 |

B. Examples according to the prior art (comparative tests)

EXAMPLE 11

6.15 parts of a high molecular sodium carboxymethylcellulose are dissolved in 315 parts of water, 450 parts of 30% strength aqueous formaldehyde solution are added, and the mixture is adjusted to pH = 7 with dilute sodium hydroxide solution and warmed to 70°C. 180 parts of urea are added and condensation effected for 2 hours at pH = 7.

The obtained precondensate solution is divided in three parts. According to Examples 1 to 4 of U.S. Pat. No. 2,797,201 these three parts are mixed with the following blowing agents:

| a) | in part 1 of the mixture | 2.12 parts of ammonium carbonat |
|---|---|---|
| b) | in part 2 of the mixture | 2.12 parts of ammonium nitrate |
| c) | in part 3 of the mixture | 2.12 parts of dinitrosopenta-methylenetetramine |

The mixtures are sprayed in a spray drier of Pyrex glass. The resulting white powders are characterized in the Table 5.

Table 5

| No. | a | b | c |
|---|---|---|---|
| Yield | 72.5 | 71.5 | 73.0 |
| Apparent specific gravity (g/l) | 191 | 225 | 233 |
| Specific surface area (m²/g) | 0.3 | 0.6 | 0.75 |
| Volatile parts (%) | 1.9 | 2.1 | 1.7 |
| Medium particle size (Coulter Counter) | 13.9 | 12.5 | 11.5 |

The results relating to the specific surface area and to the particle size demonstrate that the teaching of U.S. Pat. No. 2,797,201 does not lead to the instant invention.

EXAMPLE 12

A urea formaldehyde polycondensate is produced according to the instruction given in Example 1 of the U.S. Pat. No. 3,118,849. The molar ratio of urea to formaldehyde is 1:1. The polycondensation occurs at pH 1 at room temperature. By lowering the pH value to 1 with 1 n HCl 300 parts of water are added. The reaction is exothermic. It is necessary to cool the mixture in an ice bath. After filtration and drying a fine powder is obtained. The specific surface area is 2.9 m²/g; volatile parts: 1.7%.

EXAMPLE 13

A urea formaldehyde polycondensate is produced according to the instruction given in Example 2 of the U.S. Pat. No. 3,118,849. This means reaction at 60°C. A fine powder is obtained. The specific surface area is 1.6 m²/g; volatile parts: 1.3%.

EXAMPLE 14

A urea formaldehyde polycondensate is produced according to the instruction given in Example 3 of the U.S. Pat. No. 3,118,849. A 5% strength aqueous dimethylol-urea solution is combined at room temperature with a 1 n HCl solution, until a pH of 2.0 occurs. After 10 minutes the solution becomes turbid. Some hours later the precipitate is filtered and dried. The specific surface area is 0.9 m²/g; volatile parts: 15.2%.

EXAMPLE 15 a. Example 2 of U.S. Pat. No. 2,377,867 is carefully copied using

```
285 g urea
805 g of an aqueous formaldehyde solution
      of 37% of weight strength
 40 g malonic acid diethylester
 38 g concentrated aqueous ammonia of 28%
      of weight strength
0.2 g sodium hydroxide dissolved in 50 g
      of water
```

The batch is heated while stirring under reflux to gentle boiling at 97°C. A clear colorless solution is formed. After 30 minutes of refluxing 0.5 g of sulphamic acid are added, the batch is brought to boiling again and then cooled. It becomes opalescent at 34°C and is white and turbid at 24°C but neither a gel nor a precipitate is been formed. After 5 days standing it is possible to filter off a trace of a tacky resinous residue which is neutralized to pH = 8, washed and dried at 110°C. A glassy, hard polymer is obtained.

Neither on the sample itself nor after grinding in a high speed micronizer it is possible to determine any specific surface area when using the Ströhlein area-meter according to Haul and Dumbken [1),2)]. The tiny amount of polymer obtained is insufficient for the determination of the bulk density.
1) Chemie Ing. Technik 32 (1960) 349
2) Chemie Ing. Technik 35 (1963) 586

(b) 285 g urea
805 g 37% of weight aqueous formaldehyde and
 40 g malonic diethylester are mixed, adjusted to pH = 9 with 30% of weight caustic soda solution and refluxed for 30 minutes. On cooling down a haze becomes apparent at 45°C. The pH = 4.0 is adjusted by means of a 10% of weight aqueous sulphamic solution. The reaction mixture remains liquid, on the next day a certain increase in viscosity becomes apparent. After 5 days the formation of a hard block is observed. The block is comminuted, slurried up with water, neutralized to pH = 8.0 with a 10% of weight sodium carbonate solution, filtered, dried at 110°C and ground. 265 g of a white condensation polymer are obtained having a bulk density of 738 g/l and a specific surface area of 3.4 m²/g.

CONCLUSION

Owing to the fact that in test (a) practically no solid polymer having a surface area was obtained the process described in U.S. Pat. No. 2,377,867 is not operational for manufacturing highly dispersed, particulate urea formaldehyde polymer. When adjusting pH = 4 with sulphamic acid solution one is just entering the operational area of the present case although still being away from industrially feasible operating conditions.

What is claimed is:
1. An insoluble, infusible, finely dispersed, non-porous urea-formaldehyde condensation product in particulate form having a specific surface area of more than 10 m²/g and an average particle size smaller than 5 microns.
2. The polycondensation product as claimed in claim 1 in which the specific surface area ranges from about 10 to about 73 square meters per gram.

3. The polycondensation product as claimed in claim 1 in which the surface area ranges from about 20 to about 30 square meters per gram.

4. The polycondensation product as claimed in claim 1 in which the surface area ranges from about 25 to about 58 m²/g.

5. An insoluble and infusible finely dispersed non-porous urea-formaldehyde condensation product in the form of a white powder having a specific surface area of 73 square meters per gram and a bulk weight of 11.5 g/100 ml.

* * * * *